(12) United States Patent
Paladino et al.

(10) Patent No.: US 6,525,811 B1
(45) Date of Patent: Feb. 25, 2003

(54) METHOD AND APPARATUS FOR INSPECTING A CIRCUIT BOARD

(75) Inventors: James J. Paladino, Medway, MA (US); Bruce Gray, Walpole, MA (US); Gordon O. Barr, Somerville, MA (US)

(73) Assignee: EMC Corporation, Hopkinton, MA (US)

( * ) Notice: Subject to any disclaimer, the term of this patent is extended or adjusted under 35 U.S.C. 154(b) by 51 days.

(21) Appl. No.: 09/824,077

(22) Filed: Apr. 2, 2001

(51) Int. Cl.[7] .............................................. G01B 11/14
(52) U.S. Cl. ...................... 356/237.1; 348/126; 29/833; 358/106
(58) Field of Search ............................. 356/244, 237.2, 356/237.4, 237.5, 394, 237.1, 237.3; 348/125, 126

(56) References Cited

U.S. PATENT DOCUMENTS 5,563,703 A * 10/1996 Lebeau et al. .............. 356/237

6,043,876 A * 3/2000 Holliday et al. ......... 356/237.1

* cited by examiner

Primary Examiner—John R. Lee
Assistant Examiner—David A. Vanore
(74) Attorney, Agent, or Firm—Chapin & Huang, L.L.C.; David E. Huang, Esq.

(57) ABSTRACT

The invention is directed to techniques for inspecting a circuit board having a surface that includes at least one circuit board component. The apparatus includes a base, and a set of reflective members that includes at least one reflective member. Each reflective member of the set of reflective members is (i) supported by the base and (ii) movable relative to the base to enable that reflective member to move to an angle that reflects light from a respective portion of a circuit board component (e.g., a solder region between the component and the circuit board) in a direction away from the surface of the circuit board when the base rests on the surface of the circuit board. Since the base can rest on the surface of the circuit board, a technician does not need to hold the apparatus.

15 Claims, 8 Drawing Sheets

METHOD AND APPARATUS FOR INSPECTING A CIRCUIT BOARD

BACKGROUND OF THE INVENTION

Circuit boards typically include one or more circuit board components such as integrated circuits (ICs), resistors, capacitors, and connectors. Circuit board manufacturers often visually inspect the quality of solder joints which connect these components to the circuit boards. For example, a circuit board manufacturer may periodically examine a few circuit boards from a circuit board assembly line in order to verify that the circuit board components have been properly soldered to the circuit boards. As another example, a manufacturer may choose to rework a circuit board than scrap it. To this end, the manufacturer may unsolder an incorrect, defective or out-of-spec circuit board component from the circuit board, solder a new one in its place, and examine the resulting solder region prior to releasing the reworked circuit board from manufacturing.

Typically, a technician manually performs the inspection process. During inspection, the technician typically wishes to see a uniform and robust set of solder joints connecting each component in question to the circuit board. A healthy solder joint is generally characterized by a shiny, smooth and even appearance. Examples of poor soldering include solder joints that have a dull finish (indicative of cold solder joints), solder joints that have a granular appearance (indicative of inadequate heating), angled solder joints between misaligned or mis-registered solder pads, excessive voids between solder pads, and solder joints having solder shorts or "bridges" to neighboring pads.

There are a variety of conventional approaches to examining the solder region between a circuit board component and a circuit board. One approach (hereinafter referred to as the "handheld tool approach") involves the use of a microscope and a handheld tool. The handheld tool is similar in shape to a dental mirror in that it includes a handle and a small mirroring portion (e.g., a polished section of sheet metal) fastened to an end of the handle. A technician holds the handle and manually maneuvers the mirroring portion around the edge of the component by moving the handle. The technician views the solder region between the component and the circuit board by tilting the handle in such a way that light reflects from that solder region off of the mirroring portion through the microscope. Accordingly, the technician can examine the periphery of the solder region to either confirm proper soldering of the periphery, or identify poor or unhealthy solder joints.

Another inspection approach (hereinafter referred to as the "rework station approach") involves the use of a rework station for reworking circuit boards. A typical rework station includes a heating platform for heating the underside of a circuit board requiring rework, and an integrated positioning assembly for positioning and installing a component (e.g., an IC) onto the circuit board. The positioning assembly includes a prism assembly, a microscope, a nozzle, and a movable frame on which the prism assembly, the microscope and the nozzle are mounted. During component installation, a technician inserts the component into the nozzle, and moves the movable frame such that the nozzle and the component resides over the mounting location of the circuit board. Typically, the technician looks at the mounting location (which is typically printed with solder paste) through the microscope and the prism assembly while simultaneously operating geared knobs of the movable frame in order to precisely register the component over the mounting location. The technician then lowers the component onto the mounting location, and blows heated gas (e.g., nitrogen) over the mounting location through the nozzle in order to solder the component to the circuit board. After the technician has allowed the solder to cool, the technician can inspect the solder region by looking through the microscope and prism.

Another inspection approach (hereinafter referred to as the "computer camera" approach) involves the use of a specialized computer system having a miniature computer camera and a light source mounted to a movable frame, and a computer monitor that displays images gathered near the miniature computer camera. To inspect the solder region between a circuit board component and a circuit board, a technician operates the movable frame (i.e., moves geared knobs) to move the computer camera next to the solder region. The computer monitor then displays images of the solder region for inspection by the technician. The technician can store the image in the computer system (e.g., as a JPEG file) or, if the computer system further includes a printer, can print permanent pictures of the solder region for subsequent inspection of the solder region (e.g., for subsequent inspection by an engineer responsible for maintaining or improving the component mounting process).

It should be understood that a camera can also be used in the above-described handheld tool and rework station approaches. In particular, a camera can be mounted to the microscopes used in those approaches to take permanent pictures of soldering regions for subsequent review.

SUMMARY OF THE INVENTION

Unfortunately, there are deficiencies to the above-identified approaches to examining the solder region between a circuit board component and a circuit board. For example, if a camera is used in the conventional handheld tool approach, it is often difficult for the technician to take well-focused pictures of the solder region for subsequent review (e.g., by an engineer responsible for improving the soldering process). In particular, it is very difficult for the technician to hold the handheld tool steady so that an image of the soldering region properly reflects through the microscope while simultaneously looking through the microscope and operating the camera to take a picture. It is common for the technician to inadvertently move the handheld tool while taking the picture so that the picture is slightly out of focus thus losing details of the solder region. Accordingly, the engineer subsequently reviewing the picture will not be able to see particular features of the soldering region which were not captured by the picture. On the other hand, if a camera is unavailable, the technician would have to thoroughly document his or her findings (e.g., identify the particular corner, side or solder joint) so that the inspection process can be easily reproduced once the findings are brought to the attention of the engineer.

As another example, in the conventional rework station approach, rework station equipment is an expensive resource. If the same technician that reworks circuit boards is responsible for thoroughly inspecting the solder regions after the rework is complete, the throughput of that technician (i.e., the number of circuit boards that the technician can rework in a given period of time) can be substantially reduced and significantly increasing rework costs. Alternatively, if another technician performs the inspection process in order for the first technician to sustain maximum throughput, another rework station is needed for the other technician to perform the inspection process. The cost of rework stations can be $80K to $100K or even more depending on the sophistication of the equipment. As such, the equipment cost of the additional rework station may make the rework station approach too expensive to use for the inspection process.

As yet another example, in the conventional computer camera approach, the specialized computer system is also an expensive resource. The cost of such a system can be $30K or more. As such, the equipment cost of the specialized computer system may make the computer camera approach too expensive to use for the inspection process as well.

In contrast to the above-identified conventional inspection approaches, the invention is directed to techniques for inspecting a circuit board using an apparatus having a base that can rest on the surface of the circuit board, and reflective members for reflecting light from a circuit board component. The base of the apparatus provides improved stability over the conventional handheld tool and thus enables a technician to take clearer pictures of the circuit board component (e.g., a solder region between the component package and the circuit board) without having to struggle to hold a handheld tool steady. Additionally, using the apparatus alleviates the need for a rework station (e.g., the prism assembly, the heating platform, etc.) as needed in the rework station approach, or the need for a specialized computer system (e.g., the miniature camera, the computer monitor, etc.) as in the computer camera approach, thus enabling the equipment cost for the invention to be relatively less expensive.

One arrangement of the invention is directed to an apparatus for inspecting a circuit board having a surface that includes at least one circuit board component. The apparatus includes a base, and a set of reflective members that includes at least one reflective member. Each reflective member of the set of reflective members is (i) supported by the base and (ii) movable relative to the base to enable that reflective member to move to an angle that reflects light from a respective portion of a circuit board component (e.g., a solder region between the component and the circuit board) in a direction away from the surface of the circuit board when the base rests on the surface of the circuit board. Since the base can rest on the surface of the circuit board, a technician does not need to hold the apparatus. Accordingly, each reflective member can sit on the circuit board in a stable manner thus enabling a technician to take clear pictures of the circuit board component through one or more of the reflective members. Furthermore, using the apparatus alleviates the need for a rework station or specialized computer system to inspect the circuit board thus allowing equipment costs to remain relatively low.

In one arrangement, the base includes a set of pivot members, and each reflective member of the set of reflective members pivotally couples to a respective pivot member of the set of pivot members. Accordingly, each reflective member can pivot around a pivot member to control the view of the circuit board component.

In one arrangement, the base includes support members that contact the surface of the circuit board when the base rests on the surface of the circuit board. Accordingly, the apparatus can obtain stability from the circuit board surface without the need of a technician to hold the apparatus.

In one arrangement, each support member includes (i) an internally threaded member coupled to at least one reflective member, and (ii) a screw that screws into that internally threaded member to control a distance of that internally threaded member from the surface of the circuit board when the base rests on the surface of the circuit board. Accordingly, the position of the screws within their respective threaded members can control the height of the apparatus and thus the angles of the reflective members.

In one arrangement, the set of reflective members has a set of mirroring plates that includes at least one mirroring plate. The set of mirroring plates extend along at least a part of a periphery of the circuit board component so that each mirroring plate simultaneously reflects light from a different peripheral portion of the circuit board component when the base rests on the surface of the circuit board. Accordingly, when multiple mirroring plates are involved, the apparatus can provide views of multiple peripheral portions of the circuit board component.

In one arrangement, each mirroring plate receives light from the circuit board component at a substantially different angle and reflects that light in substantially the same direction when the base rests on the surface of the circuit board. Accordingly, a technician can view different portions of the component through a microscope without having to substantially move the microscope to view each portion.

In one arrangement, the set of mirroring plates includes exactly two mirroring plates that couple to the base so that the two mirroring plates are substantially perpendicular to each other. Accordingly, the apparatus can be placed in a corner region of any component regardless of the component size in order to view details of the solder region at the corner of that component.

In one arrangement, the set of mirroring plates includes exactly four mirroring plates that couple to the base so that the four mirroring plates substantially form the shape of a rectangle. Accordingly, the apparatus can be place around a component and adjusted so that a technician can view any peripheral portion of the solder region without having to reposition the apparatus.

The features of the invention, as described above, may be employed in circuit board manufacturing systems, devices and procedures such as those of EMC Corporation of Hopkinton, Mass.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

The invention is directed to techniques for inspecting a circuit board using an apparatus having a base that can rest on the surface of the circuit board, and reflective members for reflecting light from a circuit board component. The base of the apparatus provides improved stability over a conventional handheld tool and thus enables a technician to take clearer pictures of the circuit board component (e.g., a solder region between the component package and the circuit board) without having to struggle to hold a handheld tool steady. Furthermore, using the apparatus alleviates the need for a rework station (e.g., a prism assembly, a heating platform, etc.) as needed in a conventional rework station approach, or the need for a specialized computer system (e.g., a miniature camera, a computer monitor, etc.) as in a conventional computer camera approach, thus enabling the equipment cost for the invention to be less expensive.

Figure 1:
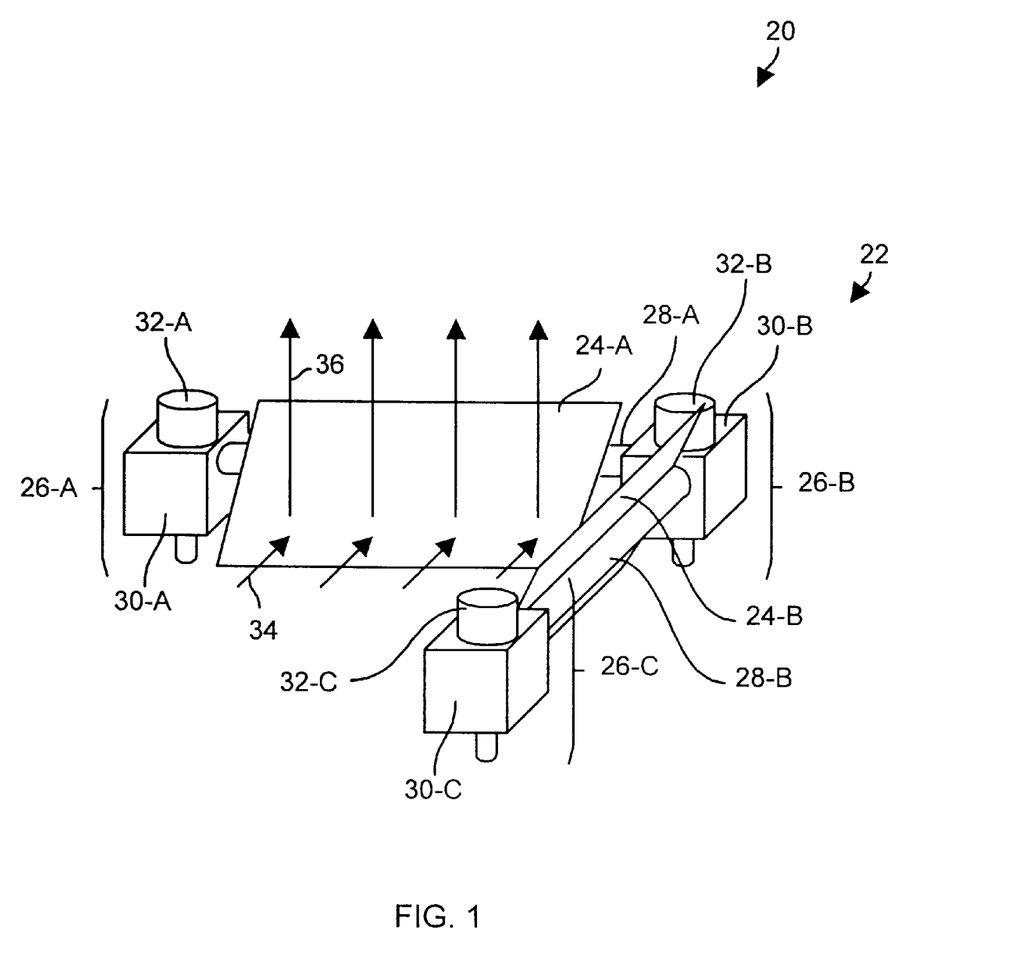
FIG. 1 is a perspective view of an inspection apparatus which is suitable for use by the invention.

FIG. 1 shows an inspection apparatus 20 which is suitable for use by the invention. The inspection apparatus 20 includes a base 22 and a set of reflective members 24-A, 24-B (collectively, reflective members 24). The base 22 includes a set of support members 26 and a set of pivot members 28. Each pivot member 28 is generally rod-shaped and extends between a pair of support members 26 in order to rigidly hold the support members 26 in place relative to each other. Each support member 26 includes an internally threaded member 30 and a screw 32 that screws into that internally threaded member 30.

As shown in FIG. 1, each reflective member 24 is supported by the base 22, and movable relative to the base 22 to enable that reflective member 24 to move to an angle that reflects light 34 away from a perspective portion of the circuit board component in a direction 36 away from the surface of the circuit board when the base 22 rests on the surface of the circuit board. In particular, each reflective member 24 pivotally couples to a respective pivot member 28 in order to rotate about that pivot member 28. For example, the reflective member 24-A is capable of rotating around the pivot member 28-A. Similarly, the reflective member 24-B is capable of rotating around the pivot member 24-B. In one arrangement, each reflective member 24-B includes a mirroring plate portion (e.g., a section of polished sheet metal).

When the apparatus 20 rests on the surface of the circuit board, the screw 32 of each support member 26 as well as the bottom edge of each reflective member 24 preferably contacts the surface of the circuit board. Accordingly, the height of the base 22 and therefore the angle of each reflective member 24 can be controlled by adjusting each screw 32 within its respective internally threaded member 30. In particular, increasing the depth of the screw 32 within its respective internally threaded member 30 increases the height of that internally threaded member 30 from the surface of the circuit board, and decreasing the depth of the screw 32 within its respective internally threaded member 30 decreases the height of that internally threaded member 30.

Preferably, a user of the apparatus 20 adjusts the screws 32 such that the base 22 is substantially level. That is, the user adjusts the screws 32 such that each of the pivot members 28 in substantially parallel with the surface of the circuit board. The depth (or height) of the screws 32 within the internally threaded members 30 ultimately dictates the pivot angle of the reflective members 24.

It should be understood that the surface of the circuit board does not need to be perfectly flat. Rather, the surface of the circuit board can include multiple circuit board components (e.g., ICs, resistors, capacitors, etc.), and any or all of the screws 32 can make contact with the components. In this situation, each screw 32 may require insertion within a respective internally threaded member 30 to a different depth (e.g., backing off one or more screws that sit on a neighboring component) in order to make the base 22 substantially level. This feature is particularly useful for circuit board manufacturers that do not provide a large clearance area (e.g., a "whiteline" or "keep-out" region of 0.200 inches) restricting how close neighboring components can be placed near the component to be examined. For example, when the apparatus 20 is placed around a circuit board component for inspection, the end of the screw 32-A may rest on a fiberglass portion of the circuit board, the end of the screw 32-B may rest on top of a neighboring IC package (e.g., a neighboring component), and the end of the screw 32-C may rest on top of a heat sink of another neighboring IC and thus requiring each screw 32 to be threaded within its respective internally threaded member 32 to a different depth in order to make the base 22 (i.e., the pit members 28) substantially level.

It should be further understood that the screws 32 are preferably made of a non-abrasive material that will not damage the surface of the circuit board such as nylon. The use of such non-abrasive material avoids introducing burrs from the screw manufacturing process that can damage the circuit board surface when turned in and out of the internally threaded member's 32 when adjusting the height of the base 22. Nylon burrs will not damage the circuit board surface. Further details of the invention will now be provided with reference to FIG. 2.

Figure 2:
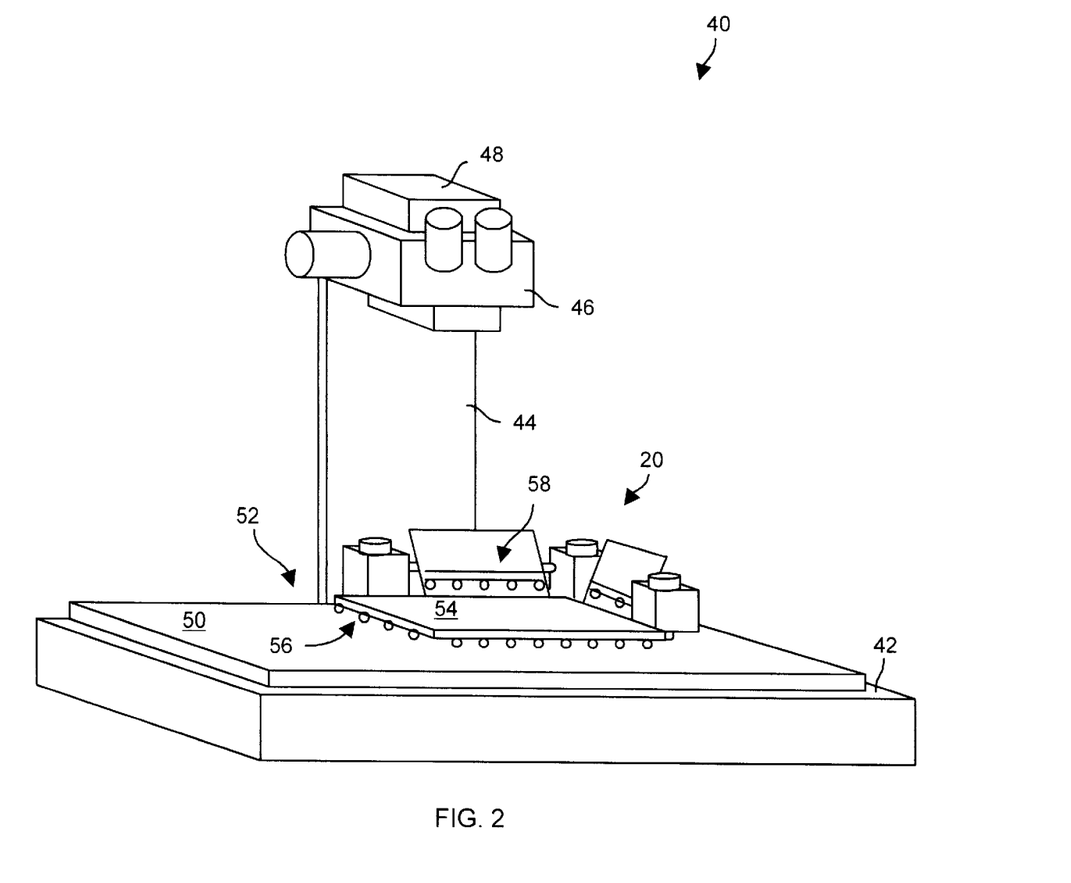
FIG. 2 is a perspective view of an inspection system which uses the inspection apparatus of FIG. 1.

FIG. 2 shows an inspection system 40 which is suitable for use by the invention.

The inspection system 40 includes the inspection apparatus 20 of FIG. 1, a foundation 42 (e.g., a stand or a base), a support arm 44, a microscope 46, and a camera 48. The support arm 44 is supported by the foundation 42. The microscope 46 and the camera 48 are in turn supported by the support arm 44. Preferably, the support arm 44 includes a mechanism (e.g., geared knobs) that enable a user to move the microscope 46 and the camera 48 toward an away from the foundation 42, as well as horizontally (i.e. in a parallel manner) relative to the foundation 42.

The inspection system 40 is capable of inspecting a circuit board 50 to having a surface 52 that includes at least one circuit board component 54. By way example only, the component 54 of FIG. 2 is a ball grid array (BGA) device. Accordingly, a solder region 56 between the BGA device and the circuit board 50 includes a set of solder balls. As shown in FIG. 2, the inspection apparatus 20 can be placed on the surface 52 of the circuit board 50 such that light from the solder region 56 reflects toward the microscope 46 and a camera 48. In particular, a user can adjust the screws 32 of the apparatus 20 (also see FIG. 1) to control the angles of reflective members 24 of the apparatus 20 and thus the direction of light from the solder region 56. Further details of the apparatus 20 will now be provided with reference to FIGS. 3 and 4.

Figure 3:
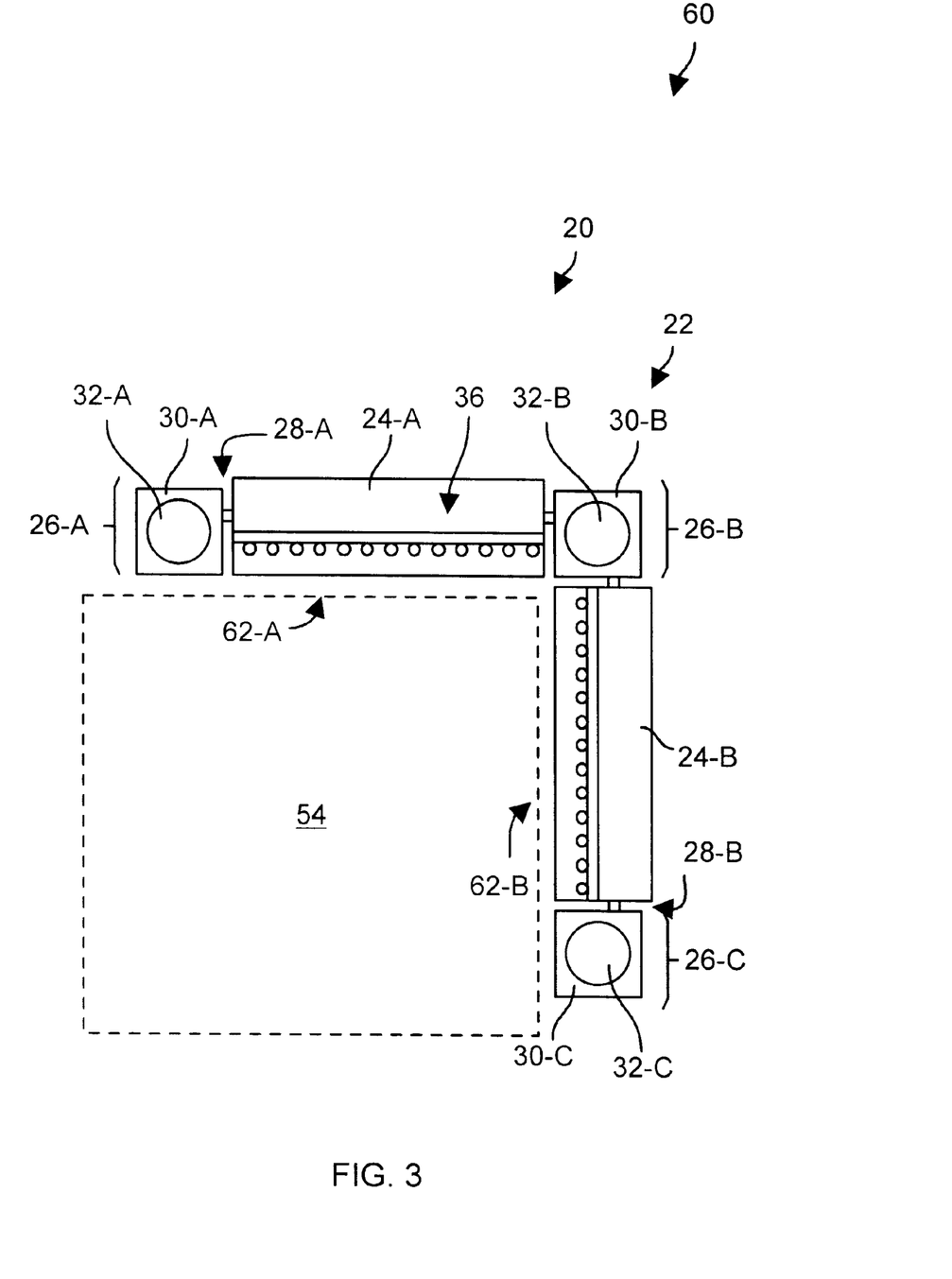
FIG. 3 is a top view of the inspection apparatus of FIG. 1.

FIG. 3 shows a top view 60 of the inspection apparatus 20 when the apparatus 20 rests on the surface of the circuit board 56 adjacent the component 54. Each reflective member 24 extends along at least part of a periphery 62 of the circuit board component 54 so that each reflective member 24 reflects light from a different peripheral portion (e.g., portion 62-A) of the circuit board component 54. Accordingly, each reflective member 24 receives light from the component 54 at a substantially different angle (e.g., the reflective member 24-*a* receives light from the portion 62-A, and the reflective member 24-B receives light from the portion 62-B) and simultaneously reflects light in the same direction (e.g. in them perpendicular direction outs of the page).

In the particular arrangement shown in FIG. 3, the apparatus 20 includes exactly two reflective members 24 which are disposed substantially perpendicular to each other. Preferably, the two reflective members 24 extend at least half the distance of the largest circuit board component 54 to be inspected using the apparatus 20 in order to enable a user to examine every external part of the periphery of the component's solder region.

Figure 4:
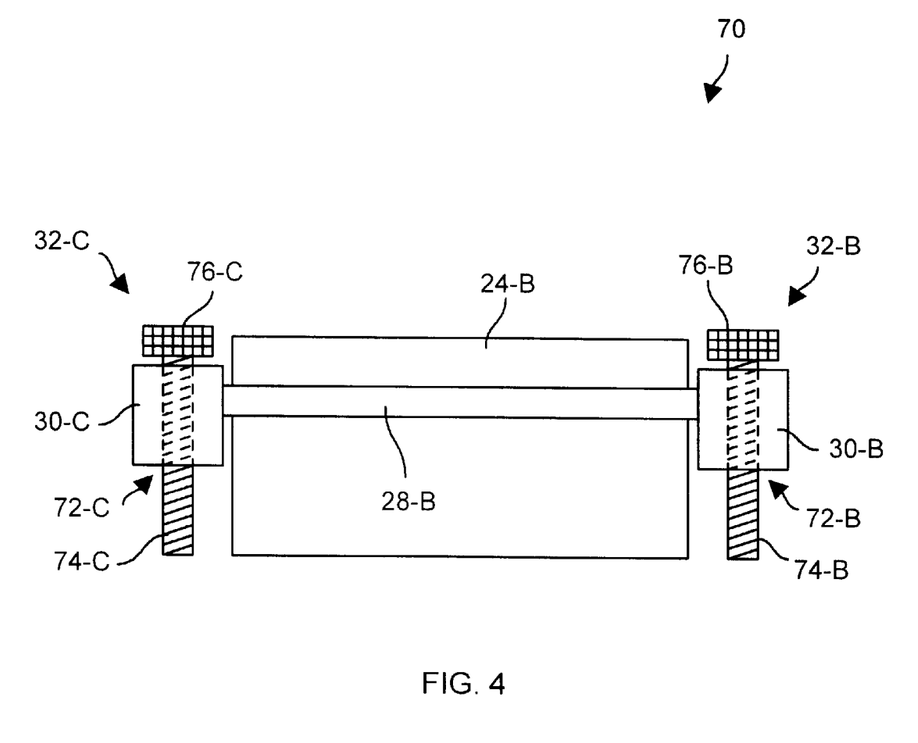
FIG. 4 is a cross-sectional side view of the inspection apparatus of FIG. 1.

FIG. 4 shows a cross-sectional side view 70 of the inspection apparatus 20. Each internally threaded member 30 defines an internally threaded cavity 72 which receives a respective screw 32. Each screw 32 includes a threaded portion 74 and a head 76. Accordingly, when a user turns the screw 32, that screw 32 moves within the internally threaded cavity 72 and relative to the other components of the apparatus 20 (e.g., the set of reflective members 24 and the set of pivot members 28). Further details of the invention will now be described with reference to FIGS. 5 and 6.

Figure 5:
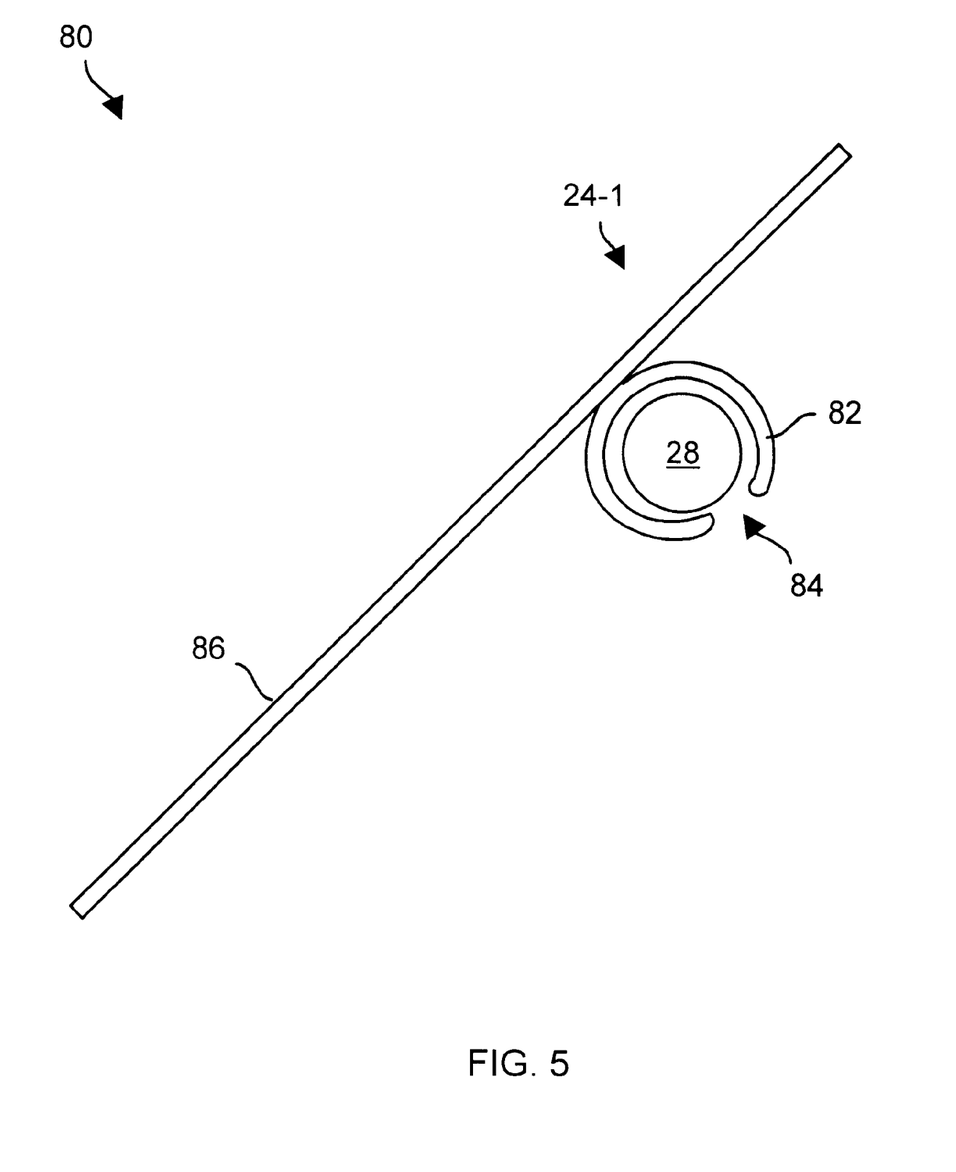
FIG. 5 is a cross-sectional side view of a reflection member and a pivot member of the inspection apparatus of FIG. 1.

FIG. 5 shows a cross-sectional side view 80 of a reflective member 24-1 which is suitable for use for each reflective member 24 of FIGS. 1 through 4. The reflective member 24-1 includes a C-shaped clip 82 which defines an opening 84, and a mirroring plate 86. The C-shaped clip 82 fastens around a pivot member 28 thus enabling the reflective member 24-1 to pivot, or rotate, about the pivot member 28. Preferably, the size of the opening 84 defined by the clip 82 is slightly smaller than the diameter of the pivot member 28 in order to prevent the reflective member 24 from easily separating from the pivot member 28 (e.g., from falling off).

Figure 6:
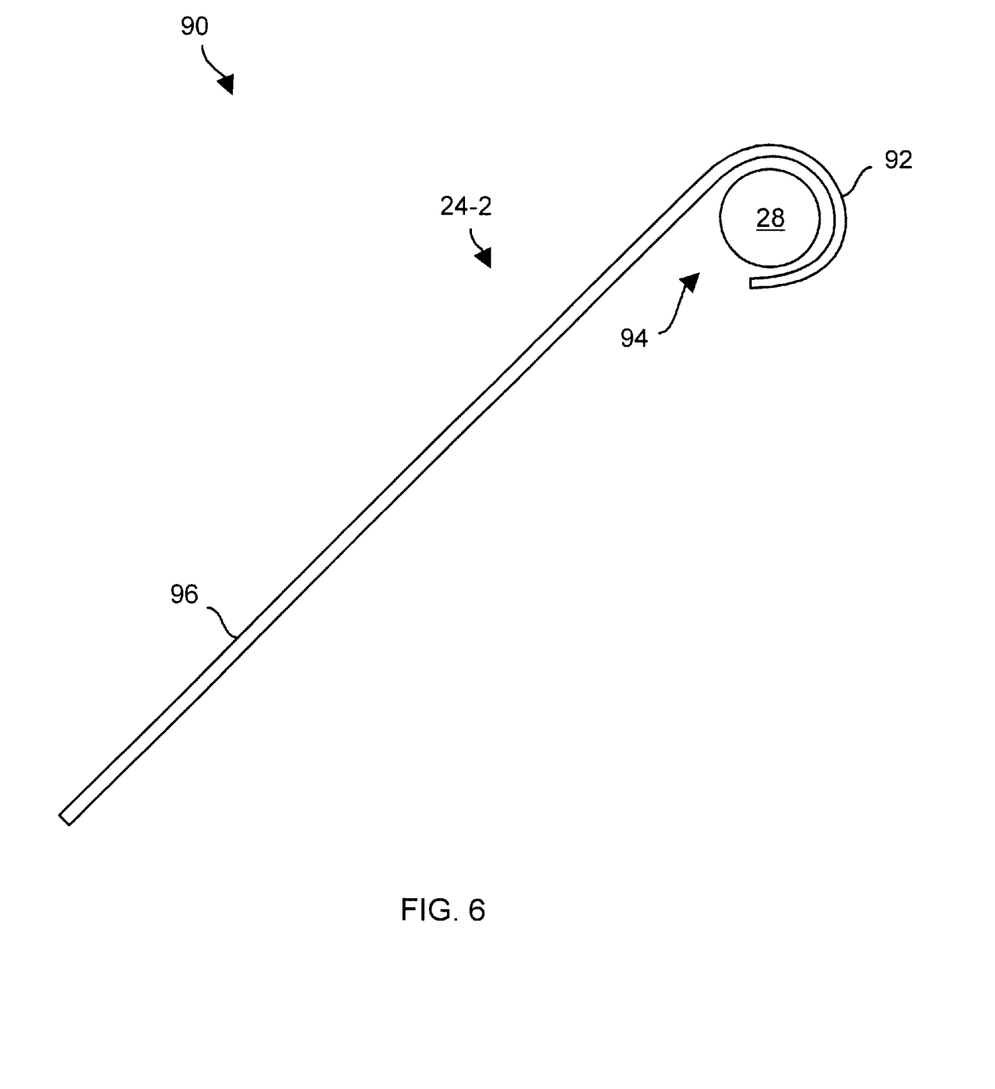
FIG. 6 is a cross-sectional side view of an alternative reflection member and the pivot member for the inspection apparatus of FIG. 1.

FIG. 6 shows a cross-sectional side view 90 of an alternative reflective member 24-2 which is also suitable for use for each reflective member 24 of FIGS. 1 through 4. The reflective member 24-2 includes a hooked portion 92 which defines an opening 94, and a mirroring plate 96. In one arrangement, the hooked portion 92 and mirroring plate 96 are formed by a single piece of thin polished metal which is bent along one edge. The hooked portion 92 enables the reflective member 24-2 to pivot about the pivot member 28 in a manner similar to that for the reflective member 24-1 FIG. 5. Preferably, the size of the opening 94 defined by the hooked portion 92 is slightly smaller than the diameter of the pivot member 28 in order to prevent the reflective member 24 from easily separating from the pivot member 28. Further details of the invention will now be provided with reference to FIG. 7.

Figure 7:
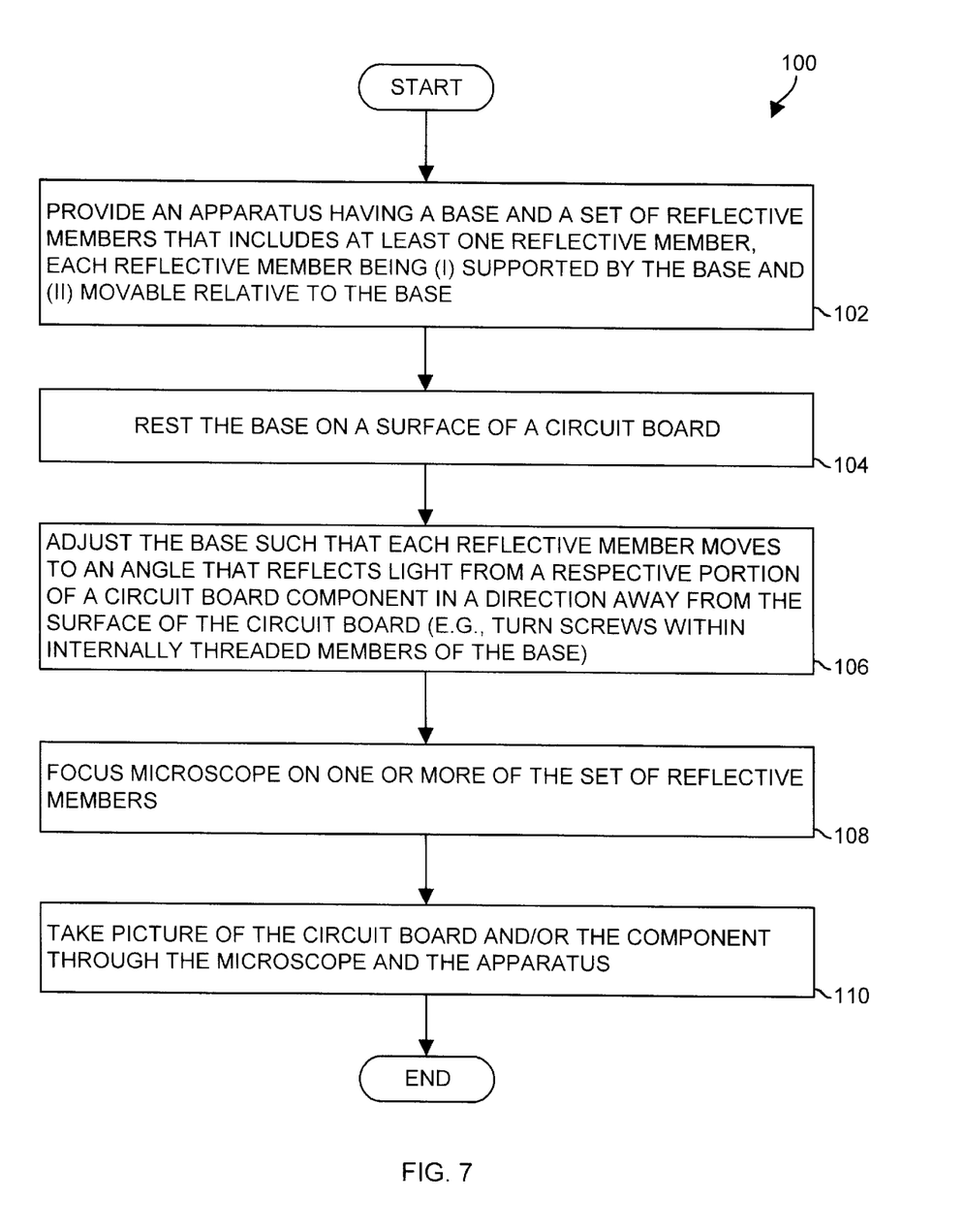
FIG. 7 is a flowchart of a procedure which is performed by a user of the inspection system of FIG. 2.

FIG. 7 shows a flowchart of a procedure 100 which is performed by a user of the inspection system 40 of FIG. 2. In step 102, the user provides the apparatus 20 having the base 22 and the set of reflective members 24 (see FIG. 1). As described above, the set of reflective members 24 includes at least one reflective member (e.g., reflective member 24-A). Each reflective member 24 is supported by the base 22 and movable relative to the base 22.

In step 104, the user rests the base 22 on the surface 52 of the circuit board 50 (see FIG. 2) . In contrast to the conventional handheld hold approach for inspecting a circuit board component which requires that a user continuously hold a handheld tool, the user is not required to continuously holds the apparatus 20.

In step 106, the user adjusts the base 22 such that each reflective member 24 moves to an angle that reflects light from a respective portion 62 (see FIG. 3) of the circuit board component 54 in a direction away from the surface 52 of the circuit board 50. In particular, the user turns the screws 32 within the internally threaded members 30 so that the base 22 is substantially level, i.e., so that the pivot members 28 of the apparatus 20 are substantially parallel to the circuit board 50. As mentioned above, if one or more of the screws 32 contact a neighboring circuit board component rather than fiberglass material of the circuit board 50, the screws 32 can be adjusted to different depths so that the base 22 is substantially level.

In step 108, the user focuses the microscope 46 (see FIG. 2) on one or more of the reflective members 28 of the apparatus 20. If higher magnifications desired, the user can focus the microscope 46 on a particular area of a single reflective member 28.

In step 110, the user takes a picture of the circuit board component 54 and/or the circuit board 50 (e.g., the solder region 56 between the component 54 and the circuit board 50) through the microscope 46 and the apparatus 20. As a result, the user can generate a clear permanent record of particular features of the circuit board 50. Since the user is not required to continuously hold the apparatus 20, the user is free to manipulate the microscope 46 and a camera 48 to clearly focus on the stable inspection apparatus 20 resting on the surface 52 of the circuit board 50. Furthermore, use of the apparatus 20 alleviates the need for expensive equipment such as a rework station used in the conventional rework station approach, and a specialized computer camera used in the conventional computer camera approach. Accordingly, if such equipment is available, it can be used for other dedicated tasks (e.g., rework, circuit board debugging, etc.) for maximum throughput. Further details of the invention will now be described with reference to FIG. 8.

Figure 8:
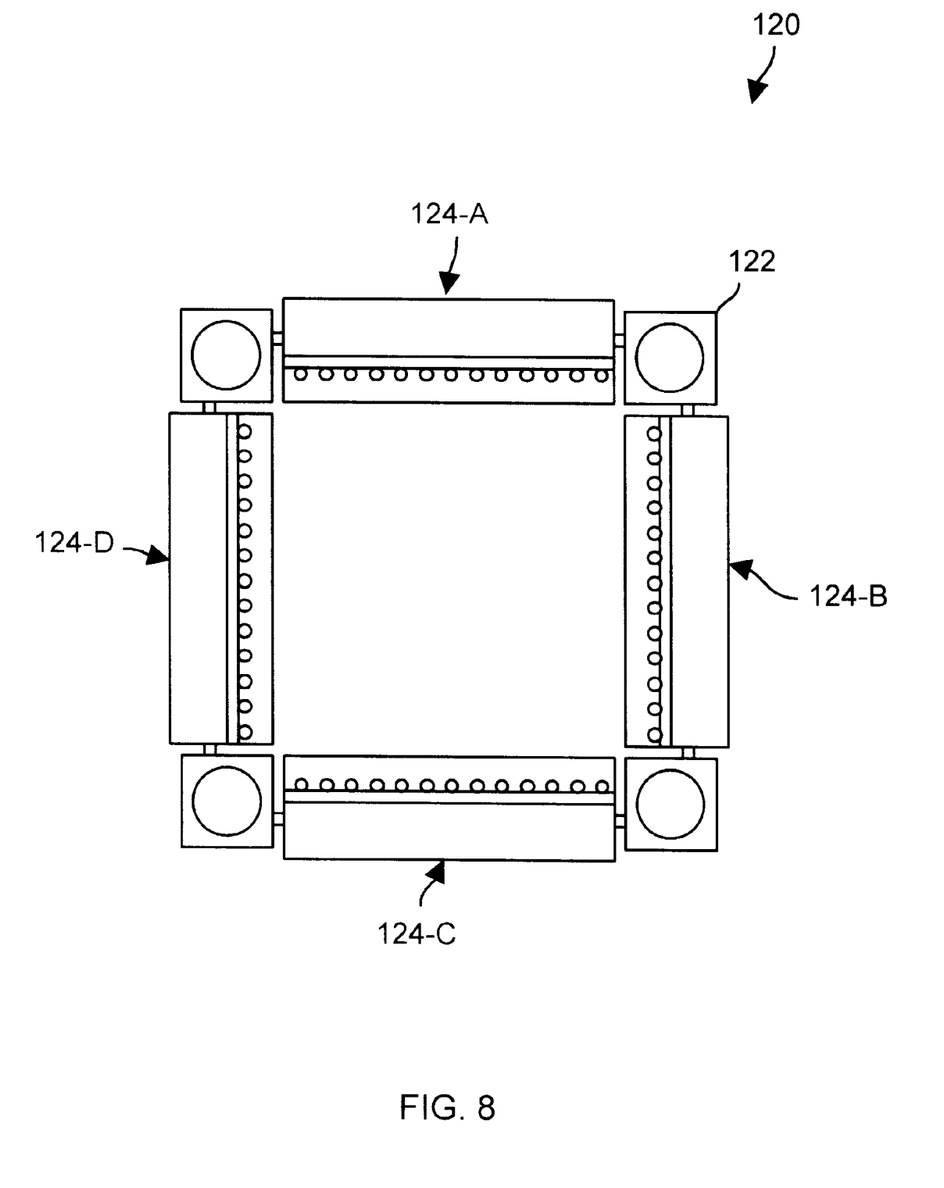
FIG. 8 is a top view of an alternative inspection apparatus to that of FIG. 1 which is suitable for use by the inspection system of FIG. 2.

FIG. 8 shows a top view of an inspection apparatus 120 which is suitable for use in the inspection system 40 of FIG. 2 in place of the inspection apparatus 20. The inspection apparatus 120 is similar to the inspection apparatus 20 (see FIG. 3). However, the inspection apparatus 120 includes a base 122 and exactly for reflective members 124 to form the shape of a rectangle. Accordingly, the apparatus 120 is well-suited for completely surrounding a circuit board component. In this arrangement, when a user has properly adjusted the inspection apparatus 120, the user can inspect any part of the solder region periphery without needing to move the inspection apparatus 120.

As described above, the invention is directed to techniques for inspecting a circuit board 50 using an apparatus 20, 120 having a base 22, 122 that can rest on the surface 52 of the circuit board 50, and reflective members 24, 124 for reflecting light from a circuit board component 54. The base 22 of the apparatus 20, 120 provides improved stability over a conventional handheld tool and thus enables a user to take clearer pictures of the circuit board component 54 (e.g., a solder region 56 between the component package and the circuit board) without having to struggle to hold a handheld tool steady. Furthermore, using the apparatus 20, 120 alleviates the need to purchase an additional and separate rework inspection station (e.g., a prism assembly, a heating platform, etc.) as needed in a conventional rework station approach, or the need for a specialized computer system (e.g., a miniature camera, a computer monitor, etc.) as in a conventional computer camera approach, thus enabling the equipment cost for the invention to be less expensive. The techniques of the invention may be used in circuit board manufacturing processes and in other manufacturing-related procedures (e.g., rework procedures) such as those of EMC Corporation of Hopkinton, Mass.

While this invention has been particularly shown and described with references to preferred embodiments thereof, it will be understood by those skilled in the art that various changes in form and details may be made therein without departing from the spirit and scope of the invention as defined by the appended claims.

For example, it should be understood that the screws 32 of the apparatus 20 were described above as being made of a non-abrasive material such as nylon. Other non-abrasive materials such as rubber and plastic are suitable for use as well. Other materials such as aluminum, steel or other metals can be used but preferably they should be coated with an insulating material (e.g., rubber) to prevent burrs.

Additionally, it should be understood that the inspection system 40 of FIG. 2 was described as including a camera 48 by way of example only and that the camera 48 is not required. A user can identify interesting features of solder regions and then document such features (e.g., make handwritten notes in a logbook, make electronic notes using a computerized input/output device, etc.) rather than take pictures of the features.

Furthermore, it should be understood that the circuit board component 54 was described above as being a BGA device by way of example only. Other types of components and mounting technologies can be examined using the apparatus 20 such as lead frame type devices, Chip Scale Packaging (CSP) technologies (e.g., flip-chip technologies, chip-on-board technologies, COBs, etc.), and the like.

Additionally, it should be understood that the reflective members 24 were described above as including a mirroring plate portion such as a section of polished sheet metal by way of example only. Other materials are suitable for use by the invention, such as reflecting foil or a glass mirroring material fastened to a thin plane-shaped backing.

Furthermore, it should be understood that the inspection system 40 can be combined or incorporated with other examination steps. For example, the system 40 can be combined with an X-ray machine or ultrasound machine for additional examination of the circuit board 50.

What is claimed is:

1. An apparatus for inspecting a circuit board having a surface that includes at least one circuit board component, the apparatus comprising:
    a base having a set of pivot members; and
    a set of reflective members that includes at least one reflective member, wherein each reflective member of the set of reflective members is (i) supported by the base and (ii) movable relative to the base to enable that reflective member to move to an angle that reflects light from a respective portion of a circuit board component in a direction away from the surface of the circuit board when the base rests on the surface of the circuit board, wherein each reflective member of the set of reflective members pivotally couples to a respective pivot member of the set of pivot members.

2. The apparatus of claim 1 wherein the base includes support members that contact the surface of the circuit board when the base rests on the surface of the circuit board.

3. The apparatus of claim 2 wherein each support member includes:
    an internally threaded member coupled to at least one reflective member; and
    a screw that screws into that internally threaded member to control a distance of that internally threaded member from the surface of the circuit board when the base rests on the surface of the circuit board.

4. The apparatus of claim 1 wherein the set of reflective members includes:
    a set of mirroring plates that includes at least one mirroring plate, the set of mirroring plates extending along at least a part of a periphery of the circuit board component so that each mirroring plate simultaneously reflects light from a different peripheral portion of the circuit board component when the base rests on the surface of the circuit board.

5. The apparatus of claim 4 wherein each mirroring plate receives light from the circuit board component at a substantially different angle and reflects that light in substantially the same direction when the base rests on the surface of the circuit board.

6. The apparatus of claim 4 wherein the set of mirroring plates includes:
    exactly two mirroring plates that couple to the base so that the two mirroring plates are substantially perpendicular to each other.

7. The apparatus of claim 4 wherein the set of mirroring plates includes:
    exactly four mirroring plates that couple to the base so that the four mirroring plates substantially form the shape of a rectangle.

8. A method for inspecting a circuit board having a surface that includes at least one circuit board component, the method comprising the steps of:
    providing an apparatus having a base and a set of reflective members that includes at least one reflective member, wherein the base includes a set of pivot members, and wherein each reflective member of the set of reflective members is (i) supported by the base and (ii) movable relative to the base;
    resting the base on the surface of the circuit board; and
    adjusting the base such that each reflective member moves to an angle that reflects light from a respective portion of a circuit board component in a direction away from the surface of the circuit board, wherein the step of providing includes the step of:
        pivotally coupling each reflective member of the set of reflective members to a respective pivot member of the set of pivot members.

9. The method of claim 8 wherein the step of resting includes the step of:
    positioning support members of the base such that each support member contacts the surface of the circuit board.

10. The method of claim 9 wherein each support member includes (i) an internally threaded member coupled to at least one reflective member, and (ii) a screw that screws into that internally threaded member; and wherein the step of adjusting the base includes the step of:
    for each support member, turning the screw of that support member within the internally threaded member of that support member to control a distance of that internally threaded member from the surface of the circuit board when the base rests on the surface of the circuit board.

11. The method of claim 8 wherein the set of reflective members includes a set of mirroring plates that includes at least one mirroring plate, and wherein the step of resting the base on the surface of the circuit board includes the step of:

placing the base on the surface of the circuit board such that the set of mirroring plates extend along at least a part of a periphery of a circuit board component so that each mirroring plate simultaneously reflects light from a different peripheral portion of the circuit board component.

12. The method of claim 11 wherein the step of adjusting the base includes the step of:

moving the base relative to the surface of the circuit board such that each mirroring plate receives light from the circuit board component at a substantially different angle and reflects that light in substantially the same direction when the base rests on the surface of the circuit board.

13. The method of claim 11 wherein the step of providing the set of reflective members includes the step of:

providing exactly two mirroring plates that couple to the base so that the two mirroring plates are substantially perpendicular to each other.

14. The method of claim 11 wherein the step of providing the set of reflective members includes the step of:

providing exactly four mirroring plates that couple to the base so that the four mirroring plates substantially form the shape of a rectangle.

15. A system for inspecting a circuit board having a surface that includes at least one circuit board component, the system comprising:

an apparatus having a base, and a set of reflective members that includes at least one reflective member, wherein each reflective member of the set of reflective members is (i) supported by the base and (ii) movable relative to the base to enable that reflective member to move to an angle that reflects light from a respective portion of a circuit board component in a direction away from the surface of the circuit board when the base rests on the surface of the circuit board, wherein the base of the apparatus includes a set of pivot members, and wherein each reflective member of the set of reflective members pivotally couples to a respective pivot member of the set of pivot members;

a microscope that receives the light reflected by each reflective member of the apparatus; and a camera mounted to the microscope that is capable of capturing images of the circuit board component through the microscope.

\* \* \* \* \*